United States Patent [19]

Kashima et al.

[11] Patent Number: 4,817,447
[45] Date of Patent: Apr. 4, 1989

[54] WEATHER RESISTANCE TESTER

[75] Inventors: Yoshio Kashima, Kasukabe; Hirofumi Kinugasa, Matsudo; Yasuo Yoshida; Teruo Iwanaga, both of Gyoda, all of Japan

[73] Assignees: Dainippon Plastics Co., Ltd., Osaka; Iwasaki Electric Co., Ltd, Tokyo, both of Japan

[21] Appl. No.: 63,641

[22] Filed: Jun. 17, 1987

[30] Foreign Application Priority Data

Jun. 17, 1986 [JP] Japan ................... 61-142153

[51] Int. Cl.$^4$ ............................................. G01N 17/00
[52] U.S. Cl. ....................................... 73/865.6; 374/57
[58] Field of Search ........................... 73/865.6; 374/57

[56]  References Cited
U.S. PATENT DOCUMENTS

| | | | |
|---|---|---|---|
| 1,827,530 | 10/1931 | Le Grand | 73/865.6 X |
| 3,327,536 | 6/1967 | Fitzgerald | 73/865.6 |
| 3,488,681 | 1/1970 | Mita et al. | 73/865.6 X |
| 3,983,742 | 10/1976 | Suga | 73/865.6 X |
| 4,012,954 | 3/1977 | Klippert | 73/865.6 X |
| 4,544,995 | 10/1985 | Suga | 73/865.6 X |
| 4,627,287 | 12/1986 | Suga | 73/865.6 |
| 4,704,903 | 11/1987 | Suga et al. | 73/865.6 |

FOREIGN PATENT DOCUMENTS

| | | |
|---|---|---|
| 13451 | 4/1980 | Japan . |
| 18743 | 4/1983 | Japan . |
| 117128 | 6/1985 | Japan . |
| 117129 | 6/1985 | Japan . |

*Primary Examiner*—Tom Noland
*Attorney, Agent, or Firm*—Cohen, Pontani & Lieberman

[57] ABSTRACT

A weather resistance tester comprising:
(a) a U.V. radiation source,
(b) a reflector,
(c) a shield panel provided in the opening of the reflector and closing the opening for transmitting U.V. radiation therethrough and substantially blocking water vapor,
(d) a sample support,
(e) temperature adjusting device,
(f) a compartment having accommodated therein the above elements (a)–(e),
(g) a recycling duct provided with a heat exchanger and blower,
(h) a humidifier and
(i) a control device for giving operational instructions to maintain a sample on the sample support at a predetermined temperature while the lamp is on and to subject the sample to a condensation condition while the lamp is off.

23 Claims, 11 Drawing Sheets

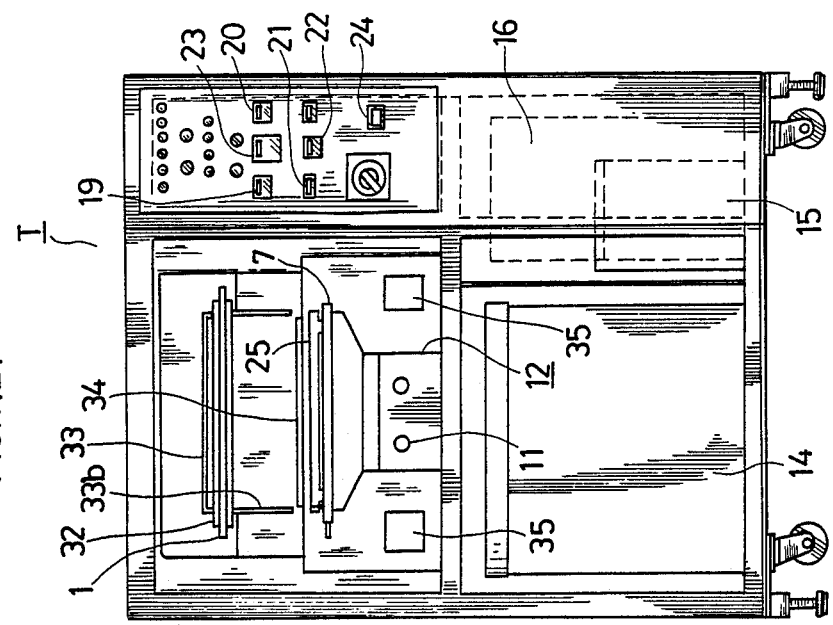
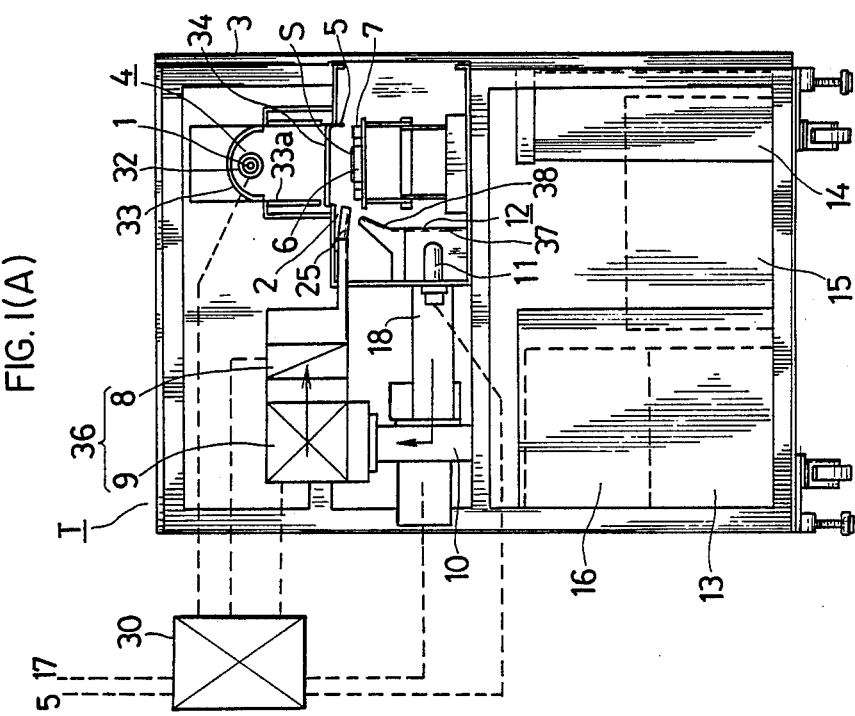
FIG.1(B)
FIG.1(A)

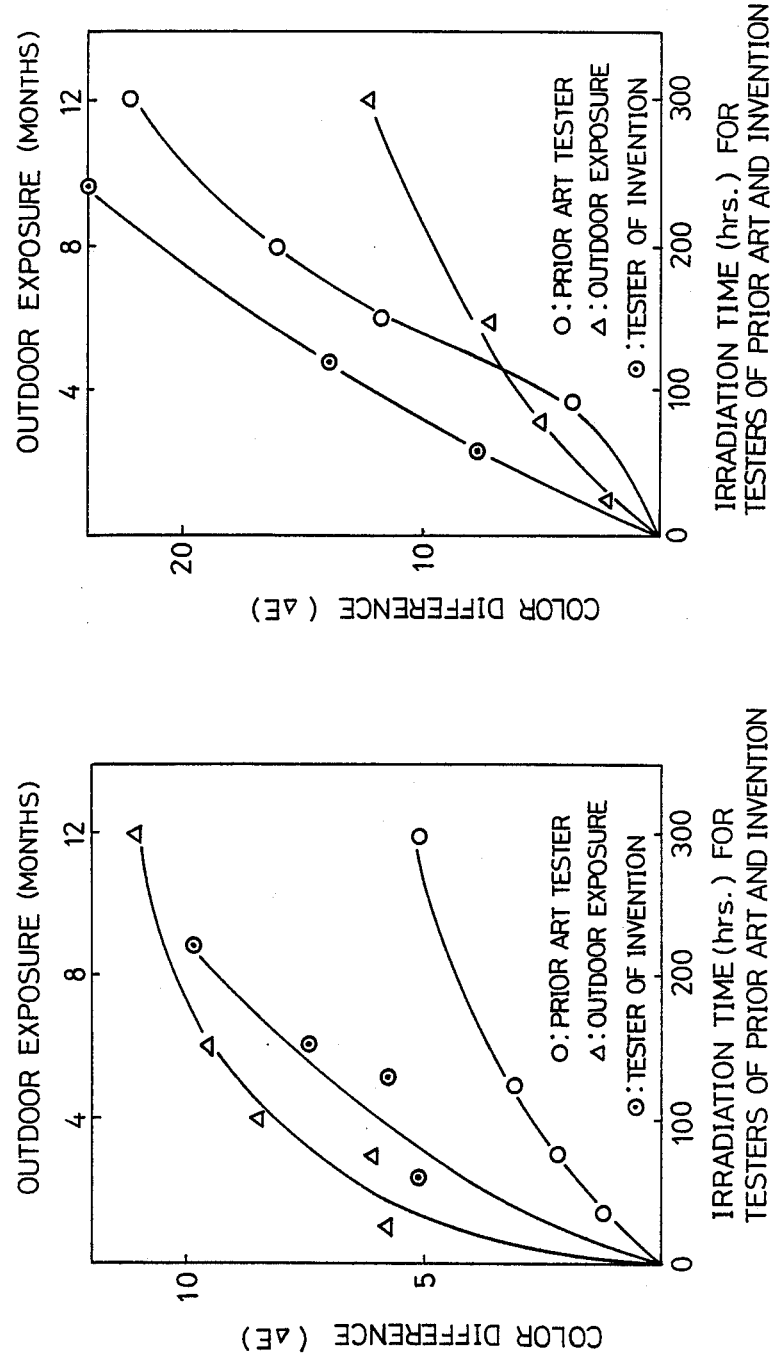

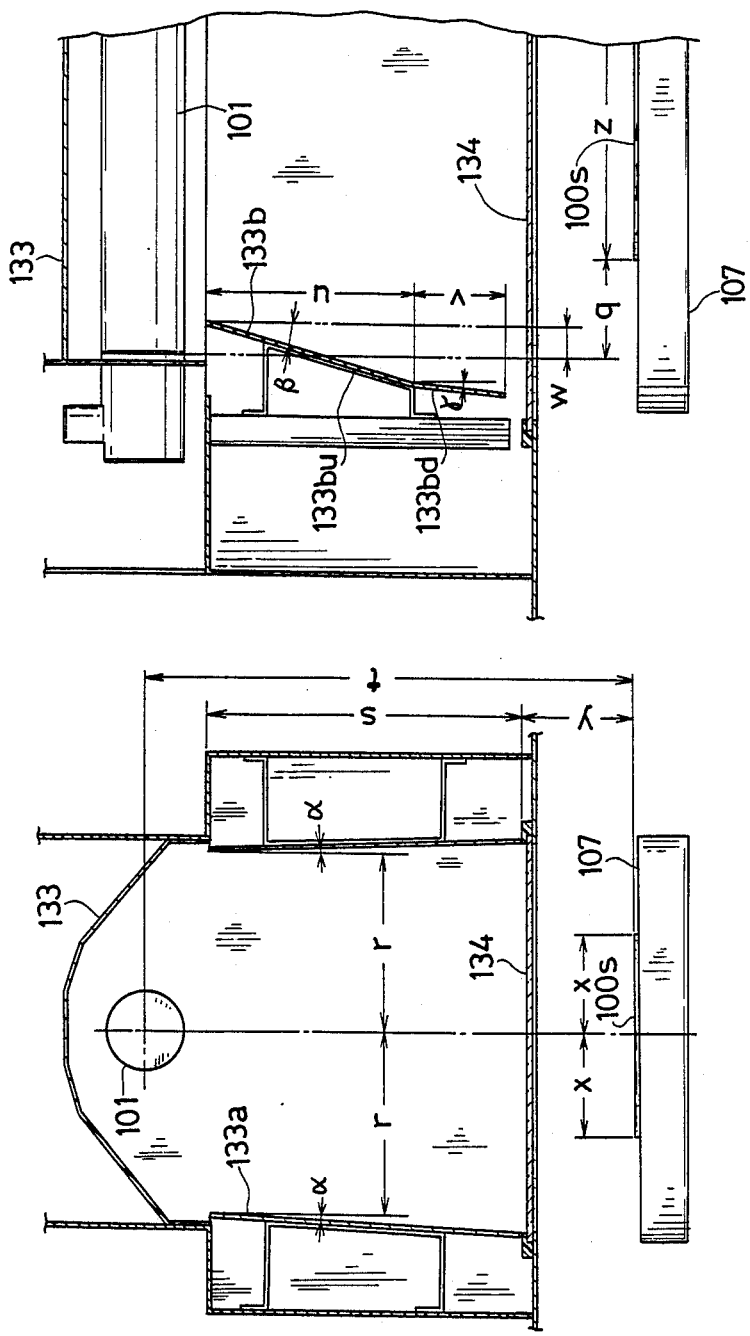

WEATHER RESISTANCE TESTER

FIELD OF THE INVENTION

The present invention relates to weather resistance testers, and more particularly to an apparatus for testing plastics, coating compositions, inks, pigments, fibers, etc. for weather resistance under conditions involving a condensation condition.

RELATED ART STATEMENT

Plastic materials, coating compositions and the like have heretofore been tested for weather resistance (lightfastness) generally by testers according to JIS B 7751-7754. Such testers usually include a carbon arc lamp, xenon arc lamp or like light source for irradiating samples with its light to perform accelerated weather resistance tests.

With these testers, however, the intensity of ultraviolet (U.V.) rays for irradiating the sample is generally about 6 mW per square centimeter of the surface to be exposed, such that the tester requires at least several hundreds of hours for determining U.V. deterioration characteristics corresponding to those resulting from a one-year exposure to sunlight.

Since it is common practice to test all the samples of individual lots, the testing procedure also requires a long period of time for determining the characteristics and evaluating the results and therefore involves the problem of extremely low efficiency.

This problem will be overcome, for example, by exposing the samples of individual lots to very intensive U.V. rays before testing for weather resistance to effect accelerated U.V. deterioration, selecting the samples to be tested from among the exposed samples according to the degree of deterioration and thereafter testing only the selected samples by the weather resistance tester. This eliminates the need to test all the samples by weathering, leading to a greatly improved testing efficiency.

We have already proposed an apparatus for pretesting the samples of individual lots before the usual weathering test, by exposing the samples to U.V. rays having a high intensity, for example, of at least about 50 mW/cm$^2$ with a metal halide lamp, whereby the samples can be checked for U.V. deterioration within a very short period of time, e.g., within up to 1/10 of the time conventionally required (see Unexamined Japanese Patent Publications SHO 60-117128 and SHO 60-117129). The pretesting apparatus is of course usable also as a weather resistance tester.

It is desired that the weathering test for plastics, coating compositions or like materials be conducted, to the greatest possible extent, under the same physical conditions as those to which the material is subjected during actual use. In the nighttime, the material in use is not only exposed to low temperatures due to the absence of sunlight but is also likely to be exposed to the condensate of water vapor.

If the conditions for the weathering test or pretesting therefor involve such a condensation condition, the result obtained will serve to provide a commercial product of improved quality as demanded by the community.

Examined Japanese Patent Publication SHO 55-13541, for example, proposes to dip the sample in water in order to subject the sample to such a condensation condition. The dipping method nevertheless in no way realizes the actual state of condensation, nor can it be a substitute therefor.

In view of this drawback, we thought it useful to adjust the temperature of the sample and the temperature and humidity of the air surrounding the sample in subjecting the sample to the actual condensation condition, and investigated whether our proposed apparatus for weathering test or pretesting could be so adapted without impairing the acceleration characteristics of the weathering test.

The condensation of water vapor is dependent generally on the temperature and the humidity. Our investigations have revealed that even if a condensate of water vapor can be deposited on the sample, some components of the apparatus other than the sample are then likely to be under the same temperature and humidity conditions as the sample, consequently becoming fogged up on condensation or locally permitting deposition of dust or the like thereon due to drops of water condensate. Thus, the condensation of water vapor is liable to produce various objections.

Especially when the cooling water jacket or reflector (mirror) for the metal halide lamp is subjected to condensation, there arises the problem that the sample will not be fully exposed to the U.V. radiation (smaller than 400 nm in wavelength, 10 to 30% of the total quantity of light) which is essential to the acceleration of weathering). While the weather resistance tester disclosed in Patent Publication No. SHO 55-13541 mentioned above has incorporated therein a xenon lamp which is originally low in the intensity of irradiating U.V. radiation (less than 400 nm in wavelength, 3.25% of the total quantity of light), the tester is totally unable to perform weathering tests in any accelerated mode if locally exposed to the condensate of water.

SUMMARY OF THE INVENTION

The present invention provides a weather resistance tester comprising:

(a) a U.V. radiation source comprising a lamp for generating U.V. radiation, (b) a reflector having the U.V. source accommodated therein and an opening at its lower portion for permitting the lamp to project U.V. radiation downward through the opening, (c) a shield panel provided in the opening of the reflector and closing the opening for transmitting U.V. radiation therethrough and substantially blocking water vapor, (d) a sample support disposed below the opening, (e) temperature adjusting means provided for the sample support, (f) a compartment having accommodated therein the U.V. source, the reflector, the shield panel, the sample support and the temperature adjusting means, (g) a duct having an intake portion and an outlet portion connected to the compartment and provided with a heat exchanger and means for blowing air, (h) a humidifier in operative relation with the sample support for providing a condensation condition therearound; and (i) control means for giving operational instructions to the U.V. source, the temperature adjusting means, the heat exchanger, the blower means and the humidifier to maintain a sample on the sample support at a predetermined temperature while the lamp is on and to subject the sample to a condensation condition while the lamp is off.

According to the present invention, the temperature adjusting means provided for the sample support and the humidifier disposed in the duct or in the compartment are operated under a specified condition through the control means to lower the temperature of the sample to a level not higher than the dew point while the lamp is off and to thereby subject the sample to a nearly natural condensation condition.

As another important feature of the present invention, the opening at the lower portion of the reflector is closed with a shield panel which permits passage of U.V. radiation therethrough but substantially blocks water vapor to partition the interior of the reflector from the other compartment portion wherein the sample is positioned. This prevents a specified portion of the tester from the condensation of water vapor that would be objectionable to the projection of U.V rays, further diminishing the pace to be controlled in temperature and humidity to assure the desired control with greater ease and improved reliability.

Since the shield panel is disposed in the same space as the sample to be exposed to water condensate, there still remains the likelihood that water vapor will condense on the shield panel. However, the sample support is provided with the temperature adjusting means as stated above, by which the temperature of the sample support only is directly adjustable to lower the temperature of the sample alone to the dew point or lower. This further reduces the likelihood of condensation on the shield panel.

When the humidifier included in the present tester is provided with a nozzle-shaped humidifying duct for guiding water vapor to a position around the sample, the shield panel can be precluded from condensation more effectively.

The shield panel used in the present invention for transmitting U.V. radiation but substantially blocking water vapor means a plate which is capable of efficiently passing therethrough the U.V. rays required for weather resistance tests and further capable of blocking water vapor (moisture).

Preferably, the shield panel is a plate, such as a thin plate of quartz glass of 1 to 4 mm in thickness, which is capable of efficiently transmitting U.V. rays, chiefly 300 to 400 nm in wavelength, and capable of efficiently blocking rays in the wavelength regions of less than 300 nm and over 400 nm.

The shield panel of the present invention may comprise a plurality of superposed plates to obtain the desired transmission characteristics when so required. For example, a thin plate of infrared absorption glass may be superposed on the above-mentioned thin plate of quartz glass for converting the infrared rays from the lamp to heat on absorption so as to effectively preclude condensation on the shield panel itself.

Further according to the present invention, the sample can be exposed to U.V. radiation with remarkably improved uniformity merely by attaching a specified auxiliary reflector to the reflector. This obviates the manual procedure, such as replacement of the sample, that would otherwise be needed.

For example, when the reflector used is dome-shaped (e.g., parabolic), the intensity of U.V. radiation irradiating the sample (surface) tends to be higher at the central portion of the sample and to be lower at the peripheral portion thereof. Especially when a spot light source or linear (elongated) light source is used as the lamp, the intensity of light on the sample surface involves variations (i.e., low uniformity), consequently necessitating the replacement of the sample to diminish variations in the test result.

The sample can be exposed to the U.V. radiation with increased uniformity by extending the main reflector partially or entirely from its lower peripheral edge downward to provide an auxiliary reflector so that the portion of the U.V. radiation which otherwise uselessly impinges on the portion around the sample is concentrically directed toward the peripheral portion of the sample.

The angle of the auxiliary reflector thus provided is of extreme importance. Preferably, the auxiliary reflector is vertical or extends downwardly outward with respect to the vertical, more preferably at an angle of 5 to 35 degrees with the vertical.

When the lamp is in the form of an elongated tube disposed horizontally, a reflector assembly is desirable which comprises a main reflector elongated along the lamp and substantially parabolic in cross section, and an auxiliary reflector comprising two lengthwise reflecting plates respectively extending downward from the lower ends of the two long sides of the main reflector and/or two widthwise reflecting plates respectively extending downward from the lower ends of the two short sides of the main reflector. Preferably the opposed reflecting plates in each pair extend downward vertically or as inclined downwardly outward away from each other at an angle with the vertical. Stated specifically, it is preferred that the lengthwise reflecting plates extend downwardly outward at an angle of 5 to 11 degrees with the vertical and that the widthwise reflecting plates extend downwardly outward at an angle of 12 to 35 degrees with the vertical.

The weather resistance tester embodying the present invention is thus adapted to expose samples to a large quantity of light energy (chiefly of U.V. energy) for causing accelerated weathering deterioration within a shortened period of time under a condensation condition which is given without impeding the application of light energy. Moreover, the light energy can be applied to the sample with improved uniformity for testing the sample with improved precision. The present tester is therefore well-suited for testing plastics, coating compositions, inks, pigments, dyes, fibers, etc. for weather resistance or for pretesting such materials before the weathering test.

BRIEF DESCRIPTION OF THE DRAWINGS

FIGS. 1 (A) and (B) are diagrams showing the construction of an embodiment of the invention;

FIGS. 3 to 7 are graphs showing variations in the color difference or gloss of samples under varying conditions;

FIG. 13 is an enlarged fragmentary diagram showing another embodiment of the invention; and FIG. 14 is an enlarged fragmentary diagram showing the second embodiment as it is seen from a different direction.

DESCRIPTION OF THE PREFERRED EMBODIMENTS

The tester of the present invention includes a lamp serving as a U.V. radiation source. Examples of useful lamps are a metal halide lamp, carbon arc lamp, xenon arc lamp, U.V. fluorescent lamp, sunlight lamp and the like, among which the metal halide lamp is preferred.

The metal halide lamp comprises a light-emitting tube made of quartz glass and having at least one pair of electrodes. The tube has enclosed therein suitable quantities of mercury and rare gas, and metal halides primarily including an iron halide or halides of iron and tin. Examined Japanese Patent Publication SHO 58-18743 discloses specific examples of such metal halide lamps.

Figure 8:
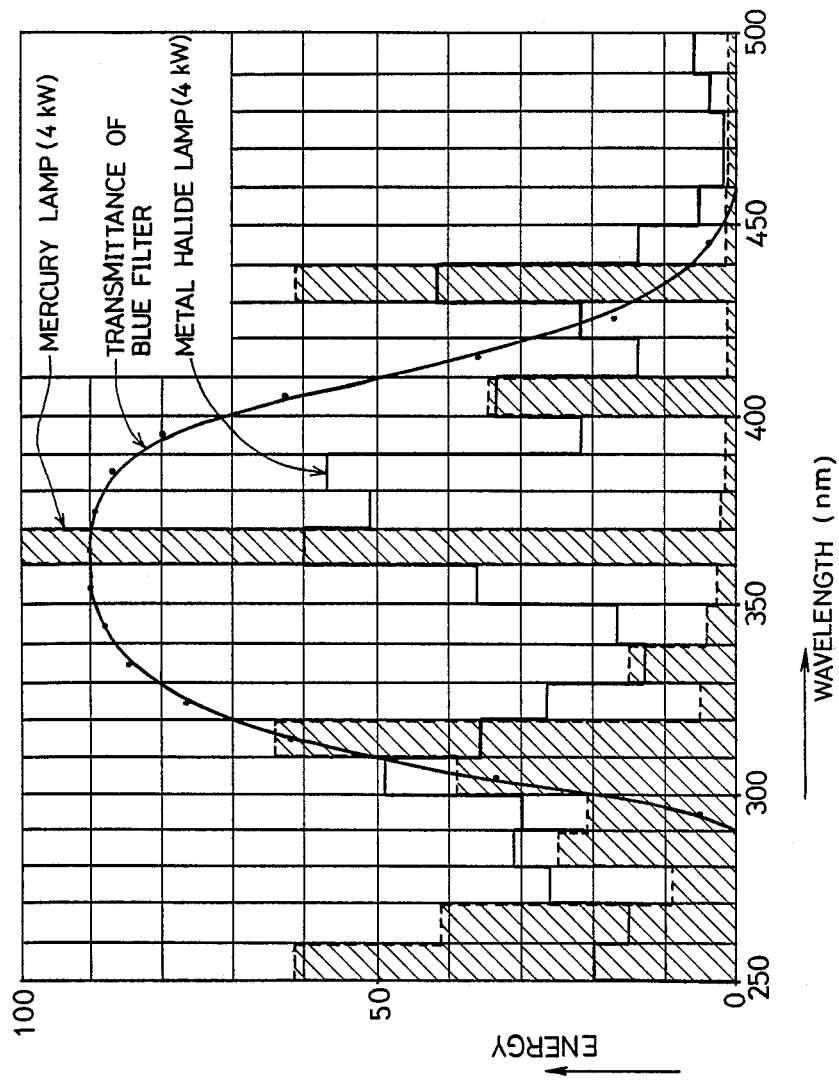
FIG. 8 is a graph showing the energy distributions of lamps and the transmittance characteristics of a filter.

The metal halide lamp, when turned on, exhibits a nearly continuous emission spectrum over the wavelength range of 300 to 400 nm as seen in FIG. 8 in comparison with a mercury lamp. Thus, the metal halide lamp has a distribution of considerably great optical energies which are predominantly available over the wavelength range of 300 to 400 nm. The lamp therefore gives samples a large quantity of light energy which causes accelerated weathering deterioration within a short period of time. More specifically stated, the sample can be exposed to U.V. rays at a high intensity of at least about 50 mW per square centimeter of the surface, with the result that the deterioration characteristics of the sample can be determined and evaluated within a greatly shortened period of time, i.e., up to 1/10 the time conventionally needed as already mentioned.

The metal halide lamp, nevertheless, invariably emits energy over the wavelength regions other than 300 to 400 nm, whereas the sunlight actually reaching the earth does not include U.V. rays of less than about 300 nm. On the other hand, the rays exceeding 400 nm in wavelength include large quantities of visible rays and infrared rays which thermally elevate the temperature of the sample and are therefore undesirable. This gives rise to the necessity of using a suitable filter in combination with the lamp to use the wavelengths of about 300 to about 400 nm only for irradiation. Examples of such filters are thin plates of low melting point soft glass, more preferably those comprising 60 to 65% (by weight, the same as hereinafter) of $SiO_2$, 15 to 20% of Pb, 7 to 8% of Na, 7 to 8% of K, 1% of Co and 1% of Ni (e.g., Blue Filter (brand name), product of Sankyo Denki Co., Ltd.). While such a filter should be suitably used in combination with the metal halide lamp, the filter, if merely disposed in the vicinity of the lamp, would be immediately broken by the heat radiated by the lamp. In actual use, therefore, the light-emitting tube is disposed in the center of a cooling water jacket, with the filter provided inside the jacket. Stated more specifically, the jacket may be in the form of a double tube comprising an inner tube and an outer tube, and the light-emitting tube is disposed inside the inner tube, with the filter provided between, the inner and outer tubes, for passing filter cooling water through the space between the inner and outer tubes. The cooling water will of course also cool the light-emitting tube.

For reference, Table 1 shows the influence of Blue Filter, mentioned above, on the U.V. radiation from some light sources. Each value listed is the intensity (W) of U.V. radiation from the light source The input to the light source is 100 W.

TABLE 1

| Light source | Wavelengths 300–400 nm | |
|---|---|---|
| | Without filter | With filter |
| Metal halide lamp | 18.9 | 11.8 |
| Mercury lamp | 10.0 | 5.8 |
| Xenon lamp | 7.3 | 3.5 |

The present invention will be described below in greater detail with reference to the embodiments shown in the drawings. The invention, however, is in no way limited by these embodiments.

Referring to FIGS. 1, 2 and 9 to 11, the weather resistance tester T shown mainly comprises a tester main body 3 having a U.V. irradiation compartment 2, a light source device 4 serving as a U.V. radiation source and provided in the interior upper portion of the compartment 2, a sample support 7 disposed below the light source device 4, a temperature adjustment recycling duct 18, a humidifier 12, a control unit 30 and a heat exchanger 36.

Figure 2:
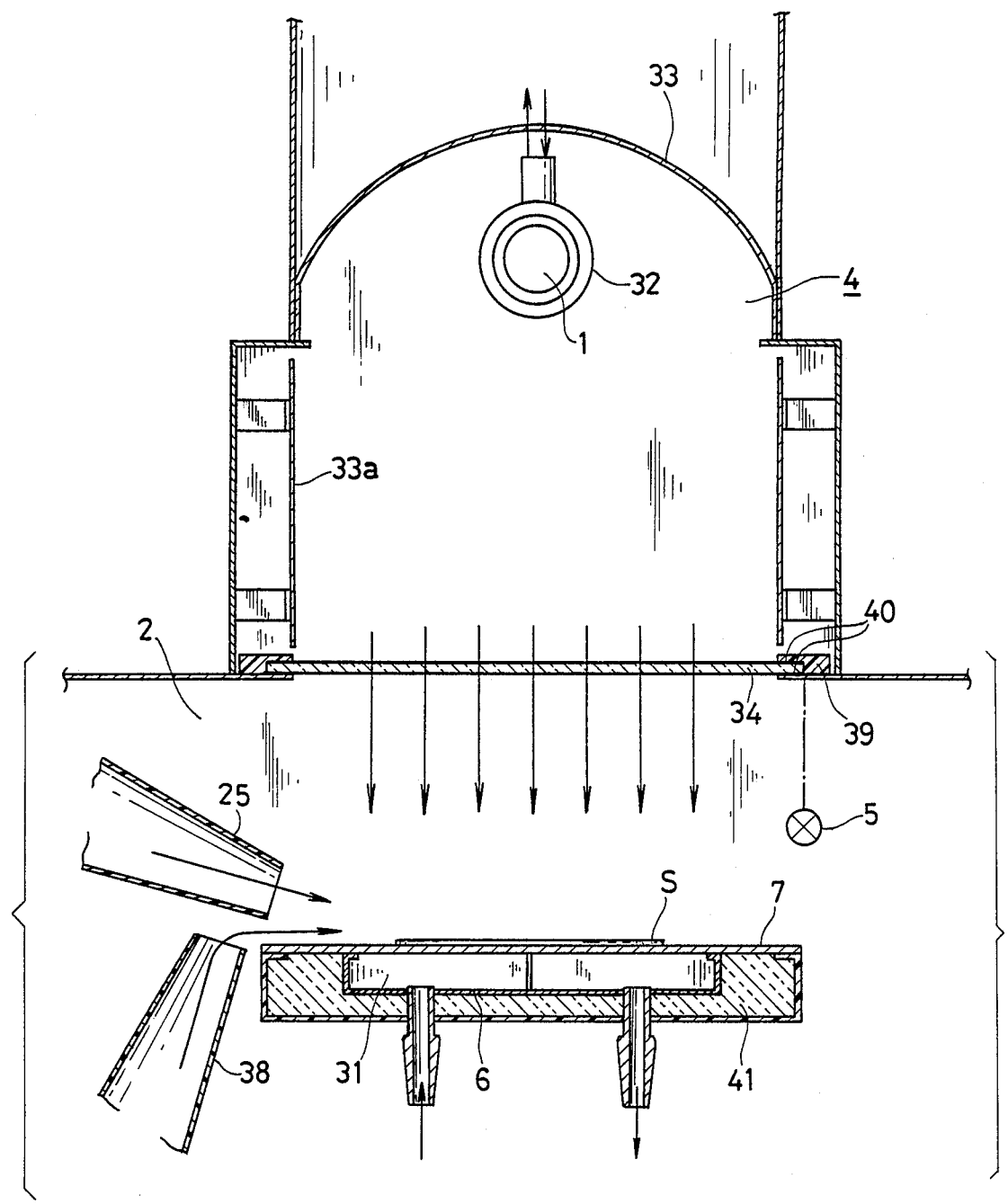
FIG. 2 is an enlarged fragmentary view showing the same.

The light source device 4, which is shown in greater detail in FIG. 2, comprises a substantially dome-shaped collimating main reflector 33, an auxiliary reflector 33a, a metal halide lamp 1 and a cooling water jacket 32 therefor which are accommodated inside the assembly of the reflectors 33, 33a, and a quartz glass plate 34 serving as a shield panel and closing an opening at the lower portion of the reflector assembly for partitioning the interior of the reflector assembly from the other portion of the U.V. irradiation compartment 2. The shield plate, i.e., the quartz glass plate 34 is capable of transmitting U.V. radiation but substantially blocks water vapor. FIG. 2 further shows a fastener 39 for the shield panel and seal packings 40.

The sample support 7 is provided with temperature adjusting means 6, which comprises a temperature sensor 17 (see FIG. 1 (A)) mounted on an upper portion of the sample support 7 for feeding a temperature signal to the control unit 30, and a cooling water recycling channel 31 provided beneath the support 7. The water channel 31 is provided with a heat exchanger 42 (FIG. 9) and a water recycling pump (not shown) which are given an operation instruction by the control unit 30. Indicated at 41 is a heat insulator.

Through the recycling duct 18, the air within the compartment 2 is partly withdrawn therefrom through intake openings 35 (see FIG. 1 (B)) of the compartment, then passed through the heat exchanger 36 and the humidifier 12 and introduced into the compartment again from a nozzle-shaped outlet 25 above the sample support 7. Indicated at 10 is a blower for the recycling duct 18. The heat exchanger 36 comprises an upstream cooling unit 9 comprising an evaporator of a refrigeration system, and a downstream heating unit 8 comprising a heater.

The humidifier 12 comprises a water tank 37, a heater 11 provided within the tank 37, a water feeder 47 (FIG. 11) for supplying water to the water tank 37 and maintaining the water at a constant level within the tank, and a humidity sensor 5. The water vapor produced is guided to a location close to a sample S on the support 7 by a humidifying duct 38 having a nozzle-shaped forward end.

Figure 9:
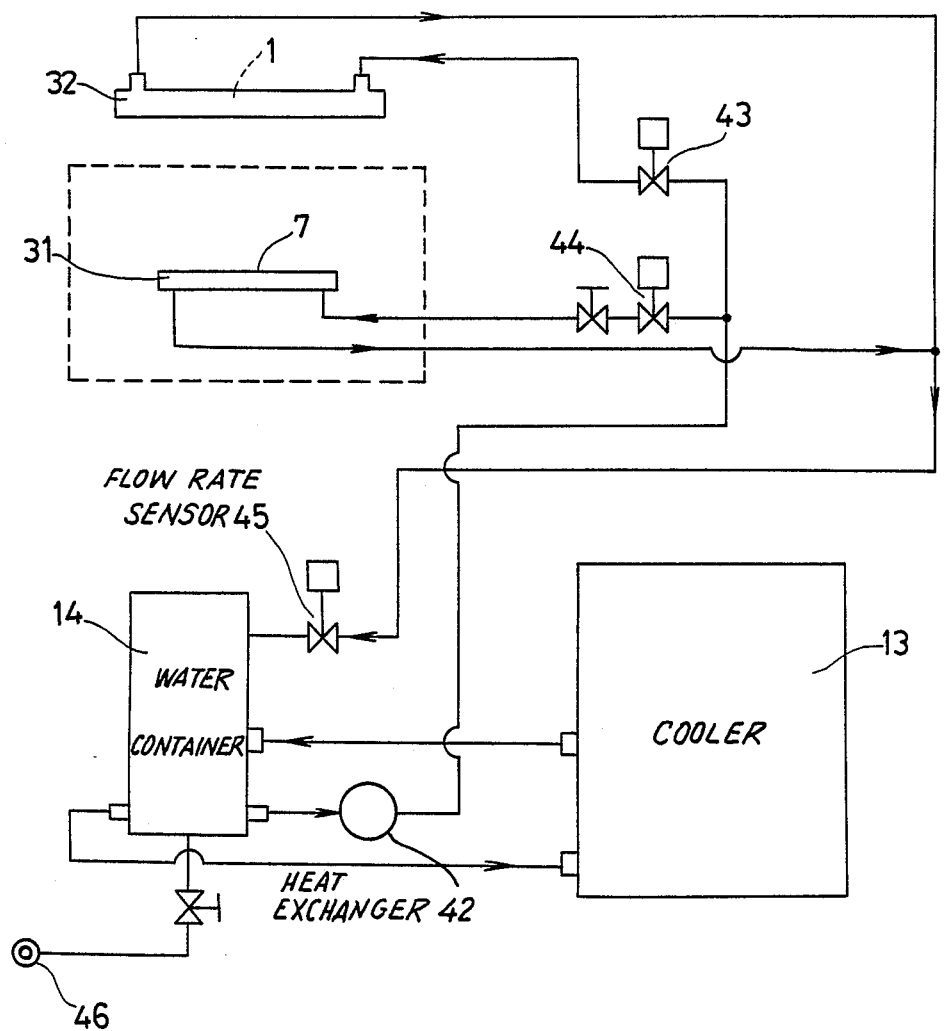
FIG. 9 is a diagram showing a cooling water circuit for the lamp and sample support of the embodiment shown in FIGS. 1 and 2.
Figure 10:
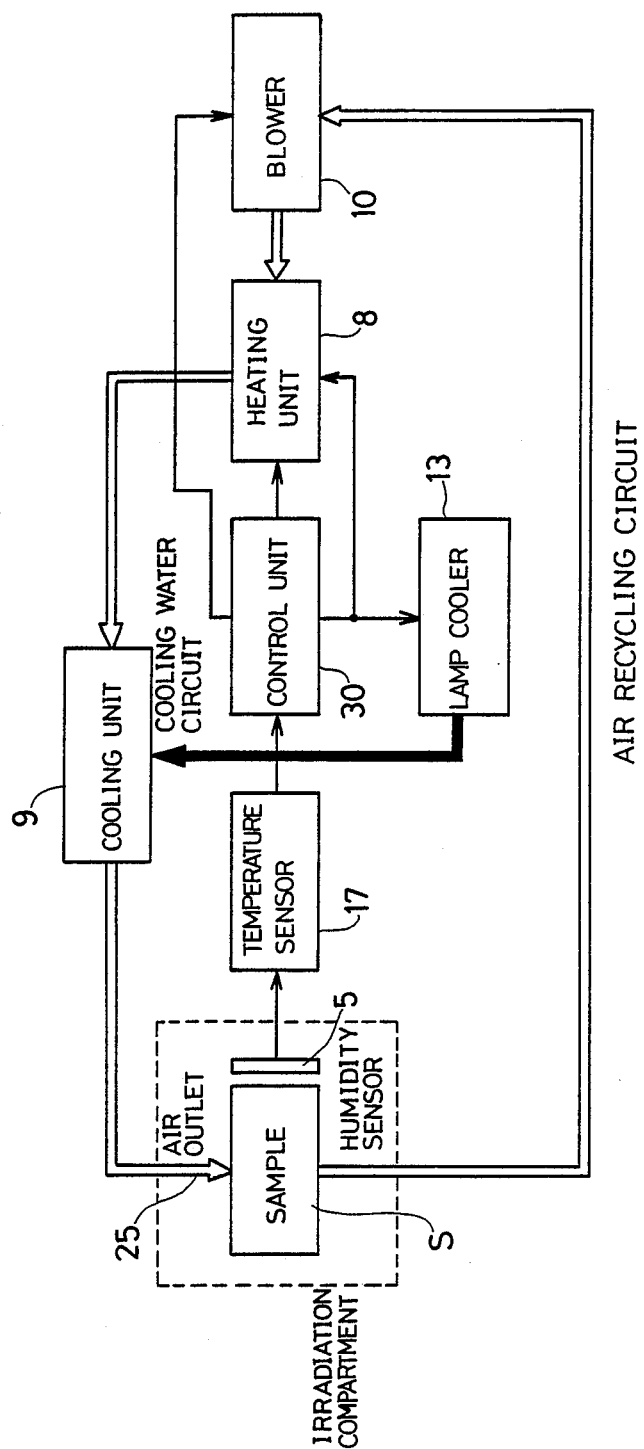
FIG. 10 is a diagram showing a temperature control circuit for the embodiment.
Figure 11:
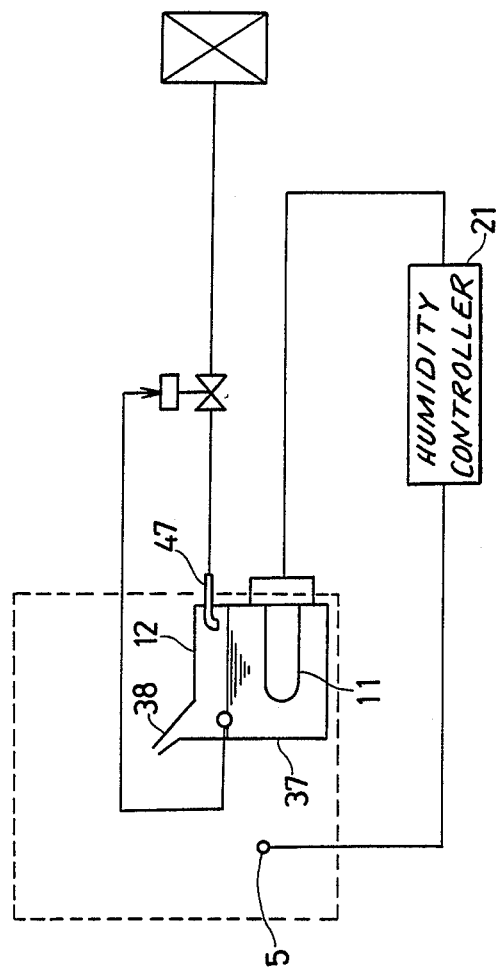
FIG. 11 is a diagram showing a humidity control circuit for the embodiment.

FIG. 1 further shows a cooler 13 for the metal halide lamp 1, a water container 14, a stabilizer 15 for the lamp 1, a refrigerator 16 for the heat exchanger 36, a lamp-on timer 19, a condensation timer 20, a humidity controller 21, a temperature controller 22, an overall testing time setting timer 23 and a U.V. radiation intensity meter 24. FIG. 9 shows a solenoid valve 43 which is energized when the lamp 1 is turned on, a solenoid valve 44 to be energized for condensation, a flow rate sensor 45 and a water drain 46.

The control unit 30 gives an operation instruction to each of the metal halide lamp 1, blower 10, heat exchanger 36, humidifier 12 and heat exchanger 42. First, the U.V. radiation source, i.e., the metal halide lamp 1 is turned on, whereby the sample S placed on the support 7 is exposed to U.V. radiation for a specified period of time (about 8 hours). During the exposure, the heat exchanger 36 and the blower 10 operate in response to a signal from the temperature sensor 17, maintaining the sample S at a specified temperature (40° to 100° C.±1.0° C.). Subsequently, the lamp 1 is turned off, terminating the U.V. irradiation. In response to signals from the temperature sensor 17 and the humidity sensor 5, the temperature adjusting means 6 and the humidifier 12 are given on-off instructions to lower the temperature of the sample S to a level not higher than the dew point and to supply hot humid air to the sample S via the recycling duct 18, permitting condensation of water vapor. (Usually, the air to be recycled has its temperature set to a level at least 5° C. higher than the temperature of the sample and has its humidity adjusted to at least 80%.) After this state has been maintained for a predetermined period of time (about 4 hours), the sample S is irradiated with U.V. radiation again in the same manner above. The cycle described is repeated (see FIG. 12 (II)).

Thus, the sample S can be subjected to a weathering test or pretested therefor within a greatly shortened period of time. Since the weather resistance test or pretest is conducted under conditions involving condensation closely resembling the condensation actually occurring during nighttime, the test can be carried out under nearly natural conditions. With the shield panel 34 of the light source device 4 closing the interior of the assembly of the reflectors 33, 33a, the cooling water jacket 32 or the specular surfaces of the reflectors 33, 33a are unlikely to become fogged up, permitting the U.V. radiation to irradiate the sample S as desired and assuring the weathering test or pretest within a short period of time.

If the assembly of reflectors 33, 33a (i.e. the lamphouse) were not closed with the shield panel 34, problems would be encountered as will be described below in detail. While the cooling water jacket 32 or the specular surfaces of the reflectors 33, 33a fog up, the interior atmosphere of the reflector assembly becomes hot and humid (30° to 80° C. in temperature, 60 to 90% in humidity), causing corrosion to the metal materials other than stainless steel inside the reflector assembly and possibly rendering the tester unusable in about a half a year. It is especially likely that the aluminum material subjected to anodic oxidation treatment and used for the reflectors 33, 33a will become corroded to result in a reduction and variations in the intensity of the irradiating U.V. radiation. While the reflector assembly includes wiring for the application of a high voltage of 1000 V and pulse voltage of about 800 V to light up the lamp, the high-temperature high-humidity condition is liable to impair the insulation for the wiring.

Figure 12:
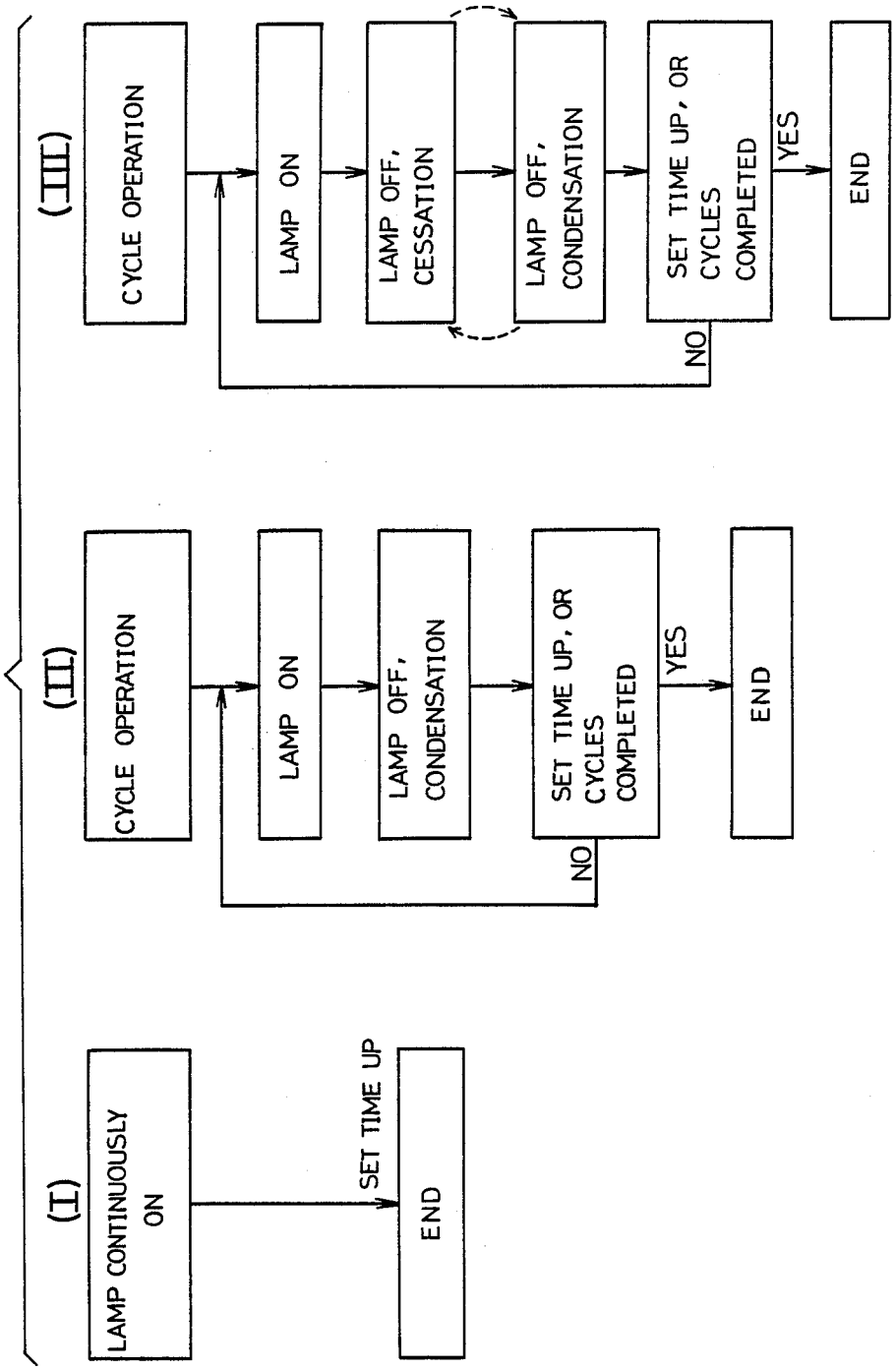
FIG. 12 is a timing chart showing exemplary operation modes of the embodiment.

Depending on the instruction of the control unit 30, the lamp can be held on continuously as shown in FIG. 12 (I) or held off to provide a condensation-free cessation period as illustrated in FIG. 12 (III).

The compartment area surrounding the sample S would be uselessly irradiated with a portion of the U.V. radiation if the main reflector 33 only is used, whereas the auxiliary reflector 33a collectively directs the radiation portion toward the peripheral portion of the sample S so as to expose the sample to the U.V. radiation with higher uniformity (uniformity on the surface of the sample, as expressed by minimum irradiation intensity/maximum irradiation intensity $\times$ 100), thereby ensuring weathering tests with improved reliability and higher reproducibility. Specifically stated, the auxiliary reflector 33a comprises a pair of lengthwise reflecting plates 33a parallel with a vertical plane through the axis of the metal halide lamp 1, and a pair of widthwise reflecting plates 33b (see FIG. 1 (B)) perpendicular to the plates 33a.

The opposed auxiliary reflecting plates in each pair, although vertical in the above embodiment, may extend downwardly outward away from each other at an angle with the vertical. For example, FIGS. 13 and 14 show an auxiliary reflector which comprises a pair of lengthwise reflecting plates 133a and a pair of widthwise reflecting plates 133b. Each widthwise reflecting plate 133b further comprises an upper segment 133bu and a lower segment 133bd which is inclined at a smaller angle than the upper segment 133bu with respect to the vertical. Thus, the lengthwise reflecting plates 133a, as well as the widthwise reflecting plates 133b, are inclined downwardly outward away from each other, with the result that even if some U.V. rays are projected around a sample 100S, U.V. rays are diffused over the peripheral portion of the sample 100S, with concentrated irradiation of the central portion thereof avoided, permitting the sample to be irradiated with the U.V. radiation with improved uniformity. In the case of the embodiment of FIGS. 13 and 14, the main reflector 133 is further sandblasted (No. 60) to provide a semidiffusion surface and obviate concentration of the U.V. radiation on the central portion of the sample 100S.

For reference, given below are the specifications of the reflectors of FIGS. 13 and 14, and the U.V. irradiation data as to the illustrated embodiment.

| $\alpha$: 8 deg | x: 50 mm | q: 50 mm | t: 240 mm |
|---|---|---|---|
| $\beta$: 15 deg | y: 55 mm | r: 88 mm | u: 101 mm |
| $\gamma$: 8 deg | z: 400 mm | s: 155 mm | v: 45 mm |
| | | | w: 15 mm |

Emission length of metal halide lamp 101: 500 mm
Average intensity of U.V. irradiation: 100 mW/cm$^2$
Uniformity: 90%

As another embodiment, unlike the first embodiment of FIGS. 1 and 2, the humidifier can alternatively be disposed within the recycling duct. The humidifier is then positioned downstream from the heat exchangers (for heating and cooling). It is further possible to conduct weathering tests under different conditions, e.g. with addition of sulfurous acid gas, ozone or the like to the air to be recycled.

Test examples are given below, in which several kinds of samples were tested for weathering resistance using the tester of FIGS. 1 and 2 according to the invention and a commercial tester to determine U.V. deterioration under conditions involving condensation.

Testers and Test Conditions (1) Tester of the invention (shown in FIGS. 1 and 2)
Lamp: Metal halide lamp, 4 kW.
Shield panel: Quartz glass (transmitting at least 90% U.V rays, 300–400 nm).
Radiation wavelength: 300–400 nm (see FIG. 8 for details).
Maximum temperature of sample surface: Up to 65° C.
Black panel temperature: 63±3° C.
U.V. radiation intensity on sample surface: 100±5 mW/cm$^2$.
Condensation cycle: The cycle of 8-hour U.V. irradiation and 4-hour condensation was repeated. Condensation was effected at sample temp. of 30° C., recycling air at temp. of at least 35° C. and humidity of at least 80%.

(2) Commercial tester (of prior art)
Brand name: Eye Super UV Tester, product of Iwasaki Electric Co., Ltd.
Lamp: Metal halide lamp, 4 kW.
Radiation wavelength: 300–400 nm (see FIG. 8 for details).
Maximum temperature of sample surface: Up to 65° C.
Black panel temperature: 63±3° C.
U.V. radiation intensity on sample surface: 100±5 mW/cm$^2$.

(3) Outdoor exposure
In Matsudo City, Chiba Pref., Japan, in January to December, 1985.

Properties Determined, and Methods of Determination (1) Changes in color difference:
Color difference (ΔE) was determined for every irradiation unit time using a color difference meter, CR-100, product of Minolta Camera Co., Ltd. and based on CIE 1976 L*a*b* color space.

(2) Changes in gloss:
Using a gloss meter, Model GM-24, product of Murakami Color Technique Lab. Co., Ltd., 60-deg specular gloss was measured.

Test Results (1) Color difference changes in ABS sheet
Sample: ABS sheet, natural, 0.8 mm in thickness.
Reference color: Y=69.07, X=0.3343, y=0.3477.
Results: Given in FIG. 3 and Table 2.

Figure 3:
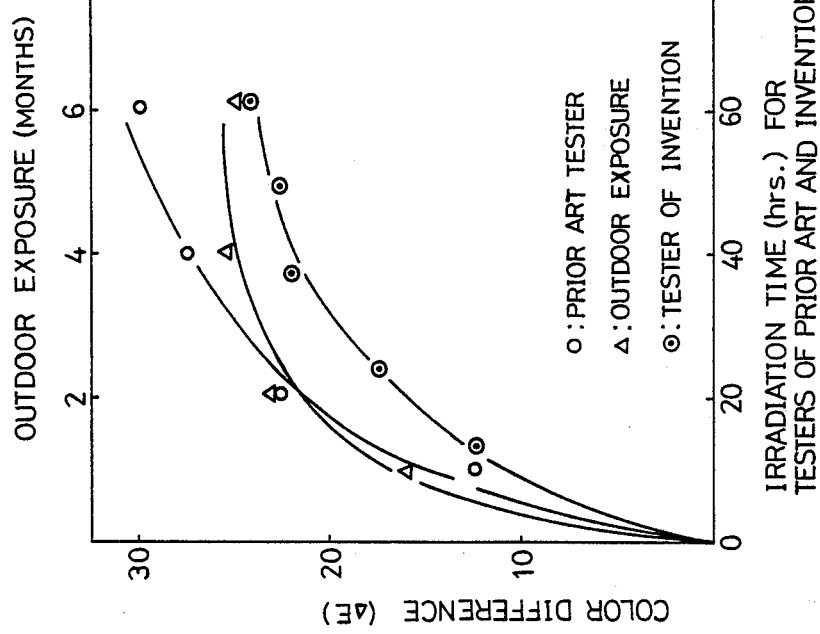

FIG. 3 reveals that the prior-art tester achieved a nearly linear change in ΔE and that due to the influence of condensation, the irradiation resulted in a reduced change in color difference in the case of the tester of the invention. This result is in good agreement with the result achieved by the outdoor exposure.

TABLE 2

| ΔE | Prior-art tester (hr) | Outdoor exposure (month) | Tester of invention (hr) | Acceleration ratio (times) |
|---|---|---|---|---|
| 5.0 | 2 | 0.15 | 4 | 27 |
| 15.0 | 10 | 0.50 | 17 | 21 |
| 20.0 | 17 | 1.60 | 30 | 38 |

The tester of the present invention achieved an average acceleration ratio of 28.7 times. The acceleration ratio listed above is expressed by:

$$\text{Acceleration ratio} = \frac{M \times 30 \text{ (days)} \times 24 \text{ (hours)}}{I}$$

wherein M is the number of months during which the sample was exposed to the weather, and I is the period (hours) of U.V. irradiation by the tester of the invention.

(2) Gloss changes in ABS sheet
Sample: The same as above (1).
Results: Shown in FIG. 4 and Table 3.

Figure 4:
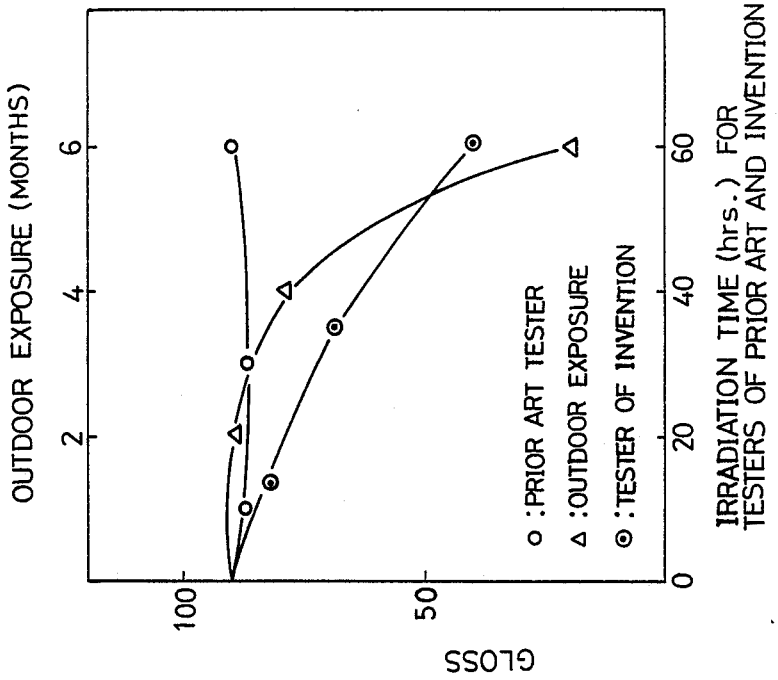

FIG. 4 reveals no reduction in gloss achieved by the prior-art tester, further indicating that a reduction occurred in 4 to 6 hours with the tester of the invention owing to the condensation condition involved.

TABLE 3

| Gloss | Prior-art tester (hr) | Outdoor exposure (month) | Tester of invention (hr) | Acceleration ratio (month) |
|---|---|---|---|---|
| 80 | — | 3.7 | 18 | 148 |
| 60 | — | 5.1 | 32 | 115 |
| 40 | — | 5.7 | 47 | 87 |

The average acceleration ratio achieved was 116.7 times.

(3) Color difference changes in yellow PP sheet
Sample: Yellow PP sheet, 0.8 mm in thickness.
Reference color: Y=71.0, X=0.4413, y=0.4673.
Results: Given in FIG. 5 and Table 4.

FIG. 5 shows that the tester of the invention produced greater changes in color difference than the prior-art tester and exhibited nearly the same tendency as the outdoor exposure.

TABLE 4

| ΔE | Prior-art tester (hr) | Outdoor exposure (month) | Tester of invention (hr) | Acceleration ratio (times) |
|---|---|---|---|---|
| 3.0 | 120 | 0.5 | 45 | 8.0 |
| 6.0 | — | 1.9 | 100 | 13.7 |
| 9.0 | — | 5.3 | 190 | 20.1 |

The average acceleration ratio achieved was 13.9 times.

(4) Color difference changes in blue PP sheet
Sample: Blue PP sheet, 0.8 mm in thickness.
Reference color: Y=14.81, X=0.1880, y=0.1755.
Results: Given in FIG. 6 and Table 5.

FIG. 6 indicates that the tester of the invention achieved greater acceleration than the prior-art tester but produced a result slightly different from the result of outdoor exposure. The difference appears attributable to a difference in the exposure ratio between irradiation and water vapor condensate.

TABLE 5

| ΔE | Prior-art tester (hr) | Outdoor exposure (month) | Tester of invention (hr) | Acceleration ratio (times) |
|---|---|---|---|---|
| 3.0 | 75 | 1.6 | 20 | 57.6 |
| 6.0 | 100 | 4.0 | 50 | 57.6 |
| 10.0 | 140 | 8.0 | 85 | 67.8 |

The average acceleration ratio achieved was 61 times.

(5) Color difference changes in red PP sheet
Sample: Red PP sheet, 0.8 mm in thickness.
Reference color: Y=13.94, X=0.4989, y=0.3173.
Results: Given in FIG. 7 and Table 6.

Figure 7:
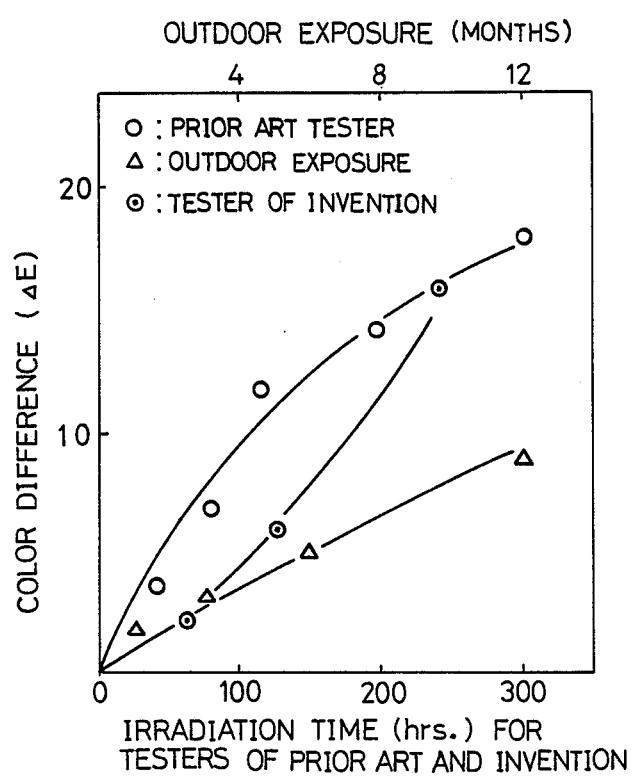

FIG. 7 reveals that the tester of the invention attained less acceleration than the prior-art tester but exhibited nearly the same tendency as the outdoor weathering.

TABLE 6

| ΔE | Prior-art tester (hr) | Outdoor exposure (month) | Tester of invention (hr) | Acceleration ratio (times) |
|---|---|---|---|---|
| 3.0 | 25 | 3.1 | 75 | 29.8 |
| 6.0 | 55 | 7.2 | 120 | 43.2 |
| 8.0 | 80 | 10.0 | 150 | 48.0 |

The average acceleration ratio achieved was 40.3 times.

According to the invention described above, the sample can be subjected to condensation of water vapor and can therefore be tested for weather resistance under nearly natural conditions. In spite of a large quantity of humid air supplied to the U.V. irradiation compartment for causing condensation, the invention precludes the cooling water jacket and the reflector surfaces from fogging, assuring weathering tests or pretests therefor within a very short period of time.

What is claimed is:

1. A weather resistance tester comprising:
   (a) a U.V. radiation source comprising a lamp for generating U.V. radiation;
   (b) a reflector having the U.V. source accommodated therein and an opening at a lower portion thereof for permitting the lamp to project U.V. radiation downward through the opening;
   (c) a shield panel provided in the opening of the reflector and closing the opening for transmitting U.V. radiation therethrough and substantially blocking water vapor therefrom;
   (d) a sample support disposed below the opening;
   (e) means for adjusting the temperature in operative relation with the sample support;
   (f) a compartment having accommodated therein the U.V. source, the reflector, the shield panel, the sample support and the temperature adjusting means;
   (g) a recycling duct having an intake portion and an outlet portion connected to the compartment and provided with a heat exchanger and means for blowing air;
   (h) a humidifier in operative relation with the sample support for providing a condensation condition therearound; and
   (i) control means for giving operational instructions to the U.V. source, the temperature adjusting means, the heat exchanger, the blower means and the humidifier to maintain a sample on the sample support at a predetermined temperature while the lamp is on and to subject the sample to a condensation condition while the lamp is off.

2. The tester as defined in claim 1 wherein the shield panel is a thin plate of quartz glass.

3. A tester as defined in claim 2, wherein the thin plate of quartz glass is 1 to 4 mm in thickness.

4. The tester as defined in claim 1, wherein the shield panel comprises a thin plate of quartz glass having a thin plate of infrared absorption glass superposed thereon.

5. The tester as defined in claim 1, wherein the humidifier comprises a water tank, a heater provided within the tank and operable in response to an instruction from the control means, and a water feeder for supplying water to the water tank and for maintaining the water at a constant level within the tank.

6. The tester as defined in claim 1, wherein the humidifier is disposed within the compartment and comprises a water tank, a heater provided within the tank and operable in response to an instruction from the control means, a water feeder for supplying a water to the tank and for maintaining the water at a constant level within the tank, and a humidifiying duct extending from the water tank toward the sample support for guiding water vapor produced in the water tank to a location close to the sample on the sample support.

7. The tester as defined in claim 1, wherein the outlet portion of the recycling duct comprises an air recycling nozzle extending from a wall of the compartment toward the sample support for guiding recycle air to around the sample on the sample support.

8. The tester as defined in claim 1, wherein the temperature adjusting means comprises a temperature sensor mounted on an upper portion of the sample support for feeding a temperature signal to the control means, and a cooling water channel provided beneath the sample support.

9. The tester as defined in claim 1, wherein the heat exchanger comprises a heater and a refrigeration cycle evaporator.

10. The tester as defined in claim 1, wherein the lamp is a metal halide lamp for emitting U.V. radiation substantially in the wavelength range of from 300 to 400 nm.

11. The tester as defined in claim 1, wherein the reflector is substantially dome-shaped.

12. The tester as defined in claim 1, wherein the reflector comprises a substantially dome-shaped main reflecting member having two long sides and two short sides and an auxiliary reflecting member extending from the lower peripheral edge of the main reflecting member downward toward the sample support.

13. The tester as defined in claim 12, wherein the auxiliary reflecting member extends from the lower peripheral edge of the main reflecting member vertically downward at an angle with the vertical.

14. The tester as defined in claim 13, wherein the auxiliary reflecting member extends downwardly outward at an angle of 5 to 35 degrees with the vertical.

15. The tester as defined in claim 12, wherein the lamp is in the form of an elongated tube disposed horizontally, and the main reflecting member is elongated along the lamp and substantially parabolic in cross section, the auxiliary reflecting member comprising two lengthwise reflecting plates respectively extending downward from the lower ends of the two long sides of the main reflecting member.

16. The tester as defined in claim 15, wherein the reflecting surface of the main reflecting member is a semi-diffusion surface.

17. The tester as defined in claim 12, wherein the lamp is in the form of an elongated tube disposed horizontally, and the main reflecting member is elongated along the lamp and substantially parabolic in cross section, the auxiliary reflecting member comprising two widthwise reflecting plates respectively extending downward from the lower ends of the two short sides of the main reflecting member.

18. The tester as defined in claim 12, wherein the lamp is in the form of an elongated tube disposed horizontally, and the main reflecting member is elongated along the lamp and substantially parabolic in cross section, the auxiliary reflecting member comprising two lengthwise reflecting plates and two widthwise reflecting plates extending downward from the lower ends of the two long sides of the main reflecting member and from the lower ends of the two short sides thereof respectively.

19. The tester as defined in claim 18, wherein each pair of the lengthwise reflecting plates extend from the lower end of the main reflecting member vertically downward at an angle with the vertical.

20. The tester as defined in claim 19, wherein each widthwise reflecting plate comprises an upper widthwise segment extending from the short side lower end of the main reflecting member downwardly outward at an angle with the vertical, and a lower widthwise segment extending from the lower end of the upper segment downwardly outward at a smaller angle than the upper segment with respect to the vertical.

21. The tester as defined in claim 20, wherein each lengthwise reflecting plate extends from the long side lower end of the main reflecting member downwardly outward at an angle of 5 to 11 degrees with the vertical, the upper widthwise segment extending from the short side lower end of the main reflecting member downwardly outward at angle of 12 to 20 degrees with the vertical, the lower widthwise segment extending from the lower end of the upper segment downwardly outward at an angle of 5 to 11 degrees with the vertical.

22. The tester as defined in claim 21, wherein each lengthwise reflecting plate extends from the long side lower end of the main reflecting member downwardly outward at an angle of about 8 degrees with the vertical, the upper widthwise segment extending from the short side lower end of the main reflecting member downwardly outward at an angle of about 15 degrees with the vertical, the lower widthwise segment extending from the lower end of the upper segment downwardly outward at angle of about 8 degrees with the vertical.

23. The tester as defined in claim 18 wherein the lengthwise reflecting plates extend from the long side lower end of the main reflecting member downwardly outward at an angle of 5 to 11 degrees with the vertical, and the widthwise reflecting plates extend from the short side lower ends of the main reflecting member downwardly outward at an angle of 12 to 35 degrees with the vertical.

* * * * *

UNITED STATES PATENT AND TRADEMARK OFFICE
CERTIFICATE OF CORRECTION

PATENT NO. : 4,817,447

DATED : April 4, 1989

INVENTOR(S) : Yoshio Kishima

It is certified that error appears in the above-identified patent and that said Letters Patent is hereby corrected as shown below:

TITLE PAGE:

[75] First inventors name should be changed from "Kashima" to --Kishima--.

Signed and Sealed this

Sixteenth Day of July, 1991

Attest:

HARRY F. MANBECK, JR.

Attesting Officer

Commissioner of Patents and Trademarks